United States Patent [19]
Kornberg et al.

[11] Patent Number: 5,111,828
[45] Date of Patent: May 12, 1992

[54] DEVICE FOR PERCUTANEOUS EXCISIONAL BREAST BIOPSY

[75] Inventors: Elliot Kornberg, Cocoa Beach, Fla.; William R. Tarello, Bethesda, Md.

[73] Assignee: PEB Biopsy Corporation, Cocoa Beach, Fla.

[21] Appl. No.: 584,614

[22] Filed: Sep. 18, 1990

[51] Int. Cl.⁵ ............................................. A61B 10/00
[52] U.S. Cl. ................................................... 128/754
[58] Field of Search ........................ 128/749, 751-754; 606/167, 170, 171

[56] References Cited

U.S. PATENT DOCUMENTS

| Re. 33,258 | 7/1990 | Onik et al. ............................ 604/22 |
| 303,290 | 9/1989 | McMenamy et al. ................ 128/753 |
| 1,275,669 | 8/1918 | Forbes . |

(List continued on next page.)

FOREIGN PATENT DOCUMENTS 2610508  8/1988  France ................. 128/751

OTHER PUBLICATIONS

Wolmark, N., "2. Biopsy as a Prelude to Definitive Operative Therapy for Breast Cancer", in Manual of Oncologic Therapeutics, edited by R. E. Wittes, 1989, pp. 8–11.
Micklos, T. J., "13. Percutaneous Biopsy Techniques", in Manual of Oncologic Therapeutics, edited by R. E. Wittes, 1989, pp. 39–42.
Donegan, W. L., "Diagnosis", in Cancer of the Breast, edited by W. L. Donegan and J. S. Spratt, 1988, Chapter 6, pp. 125, 157–158 and 162–166.
Spratt, J. S. et al., "Surgical Management", in Cancer of the Breast, edited by W. L. Donegan, and J. S. Spratt, 1988, Chapter 13, pp. 403–407 and 459–461.
Bragg, D. G., et al., "Radiologic Techniques in Cancer", in Cancer Principles & Practice of Oncology, edited by V. T. DeVita, Jr., S. Hellman and S. A. Rosenberg, Third Edition, 1989, pp. 440, 446–448, and 462.
Miller, D. L. et al., "Interventional Radiology in Oncology", in Cancer Principles & Practice of Oncology, edited by V. T. DeVita, Jr., S. Hellman, and S. A. Rosenberg, Third Edition, 1989, pp. 464–466 and 475–476.
Kinne, D. W., et al., "Physical Examination and Mammography in the Diagnosis of Breast Disease", in Breast Diseases, edited by J. R. Harris, S. Hellman, I. C. Henderson, and D. W. Kinne, 1987, pp. 77–84.
Haagensen, C. D., et al., Breast Carcinoma Risk and Detection, 1981, Chapter 26, pp. 516–525.
Wilson, R. E., "3. History and Physical Diagnosis of Breast Carcinoma", in Carcinoma of the Breast: Diagnosis and Treatment, 1983, pp. 49 and 56–58.
Annonier, C., Female Breast Examination, 1986, pp. 89–90.

Primary Examiner—Max Hindenburg
Attorney, Agent, or Firm—Beveridge, DeGrandi & Weilacher

[57] ABSTRACT

A method for percutaneous excisional breast biopsy and a percutaneous excisional breast biopsy device (PEBB device). In one variation of the method, the following steps are conducted: locating a breast lesion by radiographic techniques; positioning and implanting a localizing needle distal to said breast lesion, said localizing needle containing a hooked guide wire; positioning and implanting said hooked guide wire distal to said breast lesion; making a small incision on the surface of the breast at the point where said localizing needle enters the breast; passing a PEBB device over said localizing needle; inserting said PEBB device through said incision; further inserting said PEBB device and pushing aside the breast tissue; positioning said PEBB device to the desired location proximate said lesion; further inserting into the breast a first cutting surface of said PEBB device to the desired location distant said lesion; manipulating a second cutting surface of said PEBB device and cutting the portion of the breast tissue distal to said hooked guide wire to separate a portion of said breast tissue containing all of said lesion; and removing the PEBB device containing said lesion.

2 Claims, 4 Drawing Sheets

U.S. PATENT DOCUMENTS

| | | | |
|---|---|---|---|
| 3,087,486 | 4/1963 | Kilpatrick . | |
| 3,470,867 | 11/1964 | Goldsmith . | |
| 3,477,423 | 1/1967 | Griffith . | |
| 3,516,412 | 6/1970 | Ackerman | 128/418 |
| 3,583,390 | 6/1971 | Jascalevich . | |
| 3,587,560 | 6/1971 | Glassman . | |
| 3,605,721 | 9/1971 | Hallac . | |
| 3,628,524 | 12/1971 | Jamshidi . | |
| 3,836,776 | 9/1974 | Gullekson | 250/312 |
| 3,902,501 | 9/1975 | Citron et al. | 128/418 |
| 3,929,123 | 12/1975 | Jamshidi . | |
| 4,007,732 | 2/1977 | Kvavle et al. . | |
| 4,099,518 | 7/1978 | Baylis et al. . | |
| 4,243,048 | 1/1981 | Griffin . | |
| 4,249,541 | 2/1981 | Pratt | 128/753 |
| 4,256,119 | 3/1981 | Gauthier | 128/754 |
| 4,306,570 | 12/1981 | Matthews | 128/754 |
| 4,485,815 | 12/1984 | Amplatz et al. | 128/329 R |
| 4,532,935 | 8/1985 | Wang | 128/753 |
| 4,586,926 | 5/1986 | Osborne | 604/272 |
| 4,597,385 | 7/1986 | Watson | 128/751 |
| 4,651,752 | 3/1987 | Fuerst | 128/754 |
| 4,655,226 | 4/1987 | Lee | 128/754 |
| 4,667,684 | 5/1987 | Leigh | 128/754 |
| 4,678,459 | 7/1987 | Onick et al. | 604/22 |
| 4,691,333 | 9/1987 | Gabriele et al. | 378/37 |
| 4,708,147 | 11/1987 | Haaga | 128/753 |
| 4,727,565 | 2/1988 | Ericson | 378/205 |
| 4,766,906 | 8/1988 | Wang | 128/753 |
| 4,776,346 | 10/1988 | Beraha et al. | 128/754 |
| 4,784,134 | 11/1988 | Arana | 128/749 |
| 4,790,329 | 12/1988 | Simon | 128/749 |
| 4,793,363 | 12/1988 | Ausherman et al. | 128/754 |
| 4,799,494 | 1/1989 | Wang | 128/753 |
| 4,817,631 | 4/1989 | Schnepp-Pesch et al. | 128/753 |
| 4,832,044 | 5/1989 | Garg | 128/753 |
| 4,838,280 | 6/1989 | Haaga | 128/751 |
| 4,841,967 | 6/1989 | Chang et al. . | |
| 4,850,373 | 7/1989 | Zatloukal et al. | 128/749 |
| 4,881,550 | 11/1989 | Kothe | 128/752 |
| 4,893,635 | 1/1990 | Groot et al. | 128/754 |
| 4,917,100 | 4/1990 | Nottke | 128/749 |
| 4,919,146 | 4/1990 | Rhinehart et al. | 128/752 |
| 4,926,877 | 5/1990 | Bookwalter | 128/754 |
| 4,935,025 | 6/1990 | Bundy et al. | 128/751 |
| 4,940,061 | 7/1990 | Terwilliger et al. | 128/754 |
| 4,966,583 | 10/1990 | Debbas | 604/98 |
| 4,971,067 | 11/1990 | Boldue et al. | 128/751 |
| 4,976,723 | 12/1990 | Schad | 128/751 |
| 4,989,614 | 2/1991 | Dejter et al. | 128/752 |
| 4,991,592 | 2/1991 | Christ | 128/754 |

DEVICE FOR PERCUTANEOUS EXCISIONAL BREAST BIOPSY

BACKGROUND OF THE INVENTION

The present invention concerns a method for percutaneous excisional breast bopsy and a percutaneous excisional breast biopsy device (PEBB device).

Currently there is great emphasis on early diagnosis of breast cancer through the use of mammography since early intervention may substantially alter the course of the disease. Mammography is capable of detecting very small abnormalities, often nonpalpable, within the breast. However, mammography is usually unable to differentiate between malignant and benign lesions. Thus, the surgeon is confronted with the problem of biopsying these lesions.

The only method of making a definitive diagnosis of breast cancer is by histologic examination of the suspect tissue. There are essentially two techniques for obtaining a histologic diagnosis: open surgery biopsy and needle biopsy.

In surgical biopsy the suspect tissue is removed through a surgical incision. It can be performed under local or general anesthesia, preferable in a surgical suite. Surgical biopsies are either incisional (removal of only a part of the tumor) or excisional(removal of the entire gross tumor or lesion). Small lesions with a diameter of 1 cm or less are usually excised completely. Relative to needle biopsy, surgical biopsy has higher patient morbidity and costs.

Fine needle biopsy involves obtaining cytologic material through aspiration by a syringe and a needle. A cytologist will then examine the cytologic material. This method is not widely used since it is not efficacious. Core needle biopsy removes a small core of tissue through the use of various needles designed for this purpose (e.g., Travenol Tru-Cut needle). A pathologist will then examine the suspect tissue. With core needle biopsy a definitive diagnosis is possible only if a positive diagnosis of malignancy is made. The disadvantage of core needle biopsy is that a negative finding is inconclusive because of the possibility of being a false negative. False negatives may be due to an inadequate sample or to the wrong site being sampled. A negative finding usually requires the performance of an open biopsy. Even a positive finding may require surgical excision if conservation therapy is to be employed. The use of needle biopsy is usually restricted to tumors larger than 2 cm in diameter. Needle biopsy of smaller, mobile lesions increases the chances of obtaining a false negative.

The present invention lacks the disadvantages and shortcomings of the prior art and provides a method and device for percutaneous excisional breast biopsy.

SUMMARY OF THE INVENTION

It is an object of the present invention to provide a percutaneous excisional breast biopsy device (PEBB device) for extracting biopsy samples.

In one variation, the PEBB device includes: a cannula member having upper proximal and lower distal ends and including a cannula open at the proximal and distal ends, the cannula has a sharp cutting surface at the distal end; a stylet member having upper proximal and lower distal ends and including a stylet having a pointed distal end capable of spreading tissue, the stylet being slidable in the cannula for simultaneous insertion with the cannula, the stylet having a hollow central shaft capable of receiving a localizing needle; and an additional means of cutting tissue.

In another variation, the PEBB device includes: a cannula member having upper proximal and lower distal ends and including a cannula open at the proximal and distal ends, the cannula has a sharp cutting surface at the distal end; a stylet member having upper proximal and lower distal ends and including a stylet having a pointed distal end capable of spreading tissue, the stylet being slidable in the cannula for simultaneous insertion with the cannula, the stylet having a hollow central shaft capable of receiving a localizing needle; an additional means of cutting tissue; a localizing needle capable of being received into said stylet, the localizing needle capable of receiving a guide wire; a guide wire capable of being received into the localizing needle, the guide wire capable of holding tissue.

Various types of localizing needles and guide wires can be used with the PEBB device.

Another object of the present invention is to provide a new method to accurately locate and precisely remove a breast lesion through use of the PEBB device.

In one variation of the method, the following steps are conducted:

(a) locating a breast lesion by radiographic techniques:

(b) positioning and implanting a localizing needle distal to said breast lesion, said localizing needle containing a hooked guide wire;

(c) positioning and implanting said hooked guide wire distal to said breast lesion;

(d) making a small incision on the surface of the breast at the point where said localizing needle enters the breast;

(e) passing a PEBB device over said localizing needle;

(f) inserting said PEBB device through said incision;

(g) further inserting said PEBB device and pushing aside the breast tissue;

(h) positioning said PEBB device to the desired location proximate said lesion;

(i) further inserting into the breast a first cutting surface of said PEBB device to the desired location distal said lesion;

(j) manipulating a second cutting surface of said PEBB device and cutting the portion of the breast tissue distal to said hooked guide wire to separate a portion of said breast tissue containing all of said lesion; and (k) removing the PEBB device containing said lesion.

In another variation of the method, the following steps are conducted after the breast lesion has been located:

(a) positioning and implanting a localizing needle distal to said breast lesion, said localizing needle containing a hooked guide wire;

(b) positioning and implanting said hooked guide wire distal said breast lesion;

(c) making a small incision on the surface of the breast at the point where said localizing needle enters the breast;

(d) passing a PEBB device over said localizing needle;

(e) inserting said PEBB device through said incision;

(f) further inserting said PEBB device and pushing aside the breast tissue;

(g) positioning said PEBB device to the desired location distal said lesion;

(h) further inserting into the breast a first cutting surface of said PEBB device to the desired location near said lesion;

(i) manipulating a second cutting surface of said PEBB device and cutting the portion of the breast tissue distal to said hooked guide wire to separate a portion of said breast tissue containing all of said lesion; and (j) removing the PEBB device containing said lesion.

In yet another variation of the method, the following steps are conducted after a localizing needle and hooked guide wire have been previously implanted to the desired locations:

(a) making a small incision on the surface of the breast at the point where a localizing needle enters the breast;

(b) passing a PEBB device over said localizing needle;

(c) inserting said PEBB device through said incision;

(d) further inserting said PEBB device and pushing aside the breast tissue;

(e) positioning said PEBB device to the desired location proximate said lesion;

(f) further inserting into the breast a first cutting surface of said PEBB device to the desired location near said lesion;

(g) manipulating a second cutting surface of said PEBB device and cutting the portion of the breast tissue distal to said hooked guide wire to separate a portion of said breast tissue containing all of said lesion; and (h) removing the PEBB device containing said lesion.

Further objects of the present invention will become apparent to those skilled in the art upon a study of the following specification, appended claims, and accompanying drawings.

DETAILED DESCRIPTION OF THE INVENTION

Figure 7:
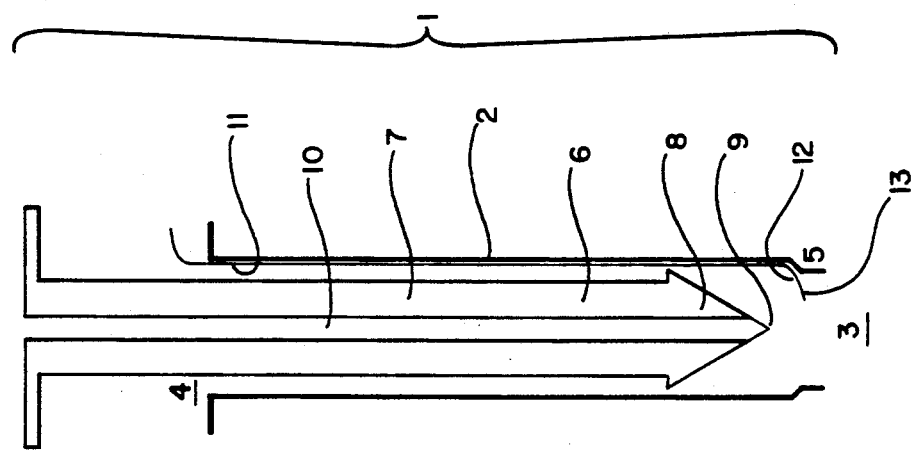
FIG. 7 is a view of the PEBB device.

With reference to FIG. 7, there is shown a PEBB device 1 which is preferably rigid. The PEBB device includes a cannula 2. Both the distal end 3 and proximate end 4 are open. The distal end 3 has a sharp cutting surface as at 5. The stylet 6 corresponds generally in shape to the cannula 2. The cylindrical shaft 7 of the stylet 6 has a tapered pointed distal puncturing end 8 which terminates in a point 9. The stylet 6 has a hollow central shaft 10 through which a localizing needle (not shown) can pass through and out the tapered pointed distal puncturing end 8. A descending element 11 fits between the cannula 2 and the stylet 6 all three elements fitting together tightly but allowing sufficient room for movement of the three elements. Descending element 11 optionally has a means at the proximate end for being rotated. The distal end 12 of the descending element 11 is a flexible steel cutting edge 13. It should be noted that the components of the PEBB device may be constructed of standard materials commonly used in the manufacture of surgical instruments. For example, stainless steel, polyurethane, suitable plastics or any other suitable surgical material may be employed. The PEBB device may be of any diameter, preferably 3 mm to 20 mm, and most preferably 10 mm. When plastics are used they can be transparent or opaque, slightly flexible or rigid.

Though the apparatus is shown as being cylindrical, other shapes are possible.

Localization techniques are necessary to identify nonpalpable abnormalities before biopsy. One technique involves use of a radiopaque hooked guide wire which has been placed through a localizing needle after the coordinates of the lesion have been determined by mammography. Virtually any imaging technique that provides three-dimensional localization of a lesion can be used to guide a localizing needle (for example, see U.S. Pat. No. 4,784,134). There are a variety of imaging techniques known in the art that can be used for needle guidance during biopsy. These techniques include fluoroscopy, ultrasound and computed tomography. Even magnetic resonance can be used with needles made from a special stainless steel. The choice of which modality to use is based on lesion size, position, and visibility; equipment availability; and the skills and preference of the individual radiologist.

Figure 1:
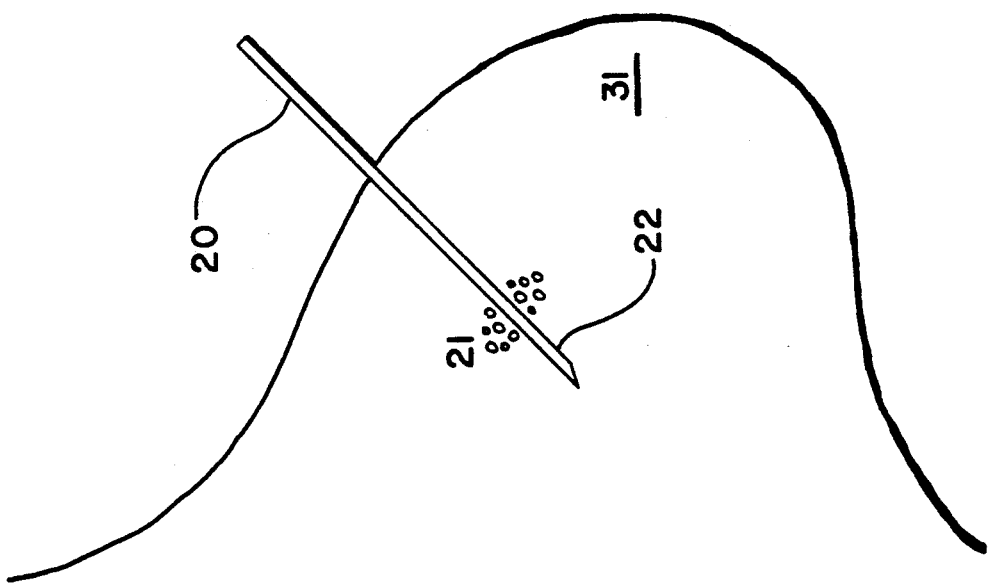
FIG. 1 is a simplified section of a human breast showing a localizing needle which has been passed distal to the breast lesion.

The hooked guide wire technique for localization of lesions is well known in the art (*Cancer of the Breast*, W.L. Donegan and J.S. Spratt, 1988, pages 157–158). Using data from previous mammograms, the localizing needle 20 in FIG. 1 is inserted into the breast 31 at the approximate site of the lesion 21 (*Breast Diseases*, edited by J.R. Harris, S. Hellman, I.C. Henderson, and D.W. Kinne, 1987, pages 82–83). Through repeated mammograms and adjustment of the needle 20, the needle tip 22 is placed through and distal to the lesion 21, where the term "distal" means a location after the lesion (i.e., under or above, depending on patient position). Standard localizing needles of various sizes can be utilized, for example 18 to 28 gauge. The choice of needle type and size depends on the size, type, and location of the lesion and the preferences of the radiologist.

Figure 2:
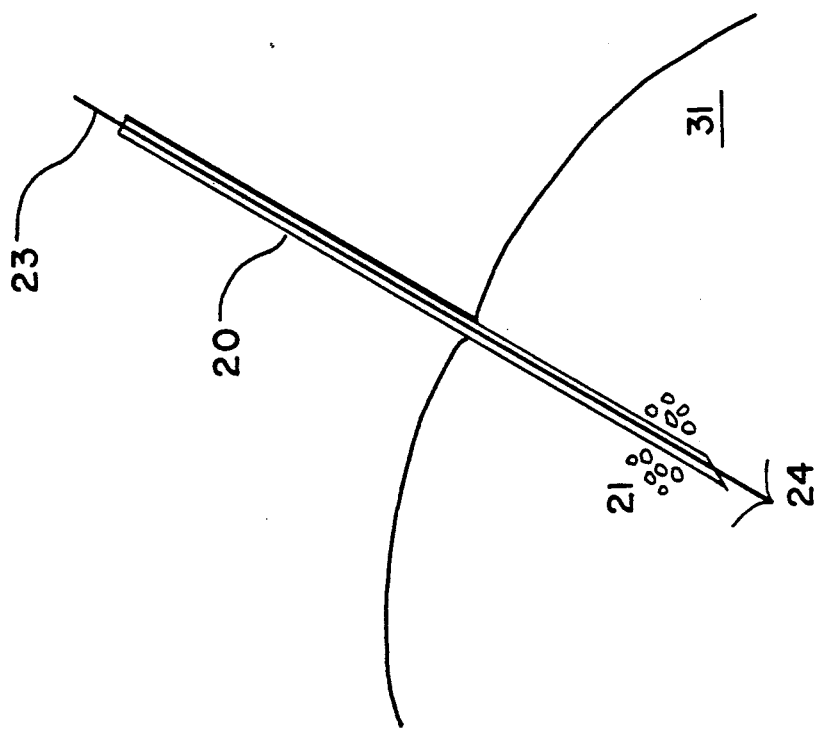
FIG. 2 is a view of the localizing needle through which a hooked guide wire has been passed.

In FIG. 2, a hooked guide wire 23 is inserted through the localizing needle 20. Preferably, the hooked guide wire 23 has been preloaded into the localizing needle 20 prior to the localizing needle being implanted into the breast. The hooked guide wire 23 is further inserted through the localizing needle 20 whereupon the hooked end 24 of the hooked guide wire 23 immediately expands. The hooked end 24 of the hooked guide wire 23 is then lodged at the desired point where it anchors itself in the surrounding breast tissue. The hooked end 2 of the hooked guide wire 23 provides a relatively stable, anchored guide and serves as a means to locate the lesion 21 when the biopsy takes place. The biopsy may be immediately conducted or it may be conducted at another time or place.

The hooked guide wire 23 may be made of steel, spring steel or any other metal which has a memory (i.e., when the hooked guide wire is place in tissue, and is no longer constrained by the localizing needle, it resumes its original form); it is radiopaque. The hooked guide wire 23 is resilient in order that it may be compressed and loaded through the localizing needle 20. The hooked guide wire is preferably preloaded in the localizing needle prior to biopsy. The hooked guide wire may be of standard length (15-30 cm) and standard size diameter.

Figure 8:
FIG. 8 is a view of a specially designed hooked guide wire.

The hooked guide wire may be of standard design or it may be as hereinafter described. The specially designed hooked guide wire may have 2 to 8 arms (FIG. 8).

Figure 3:
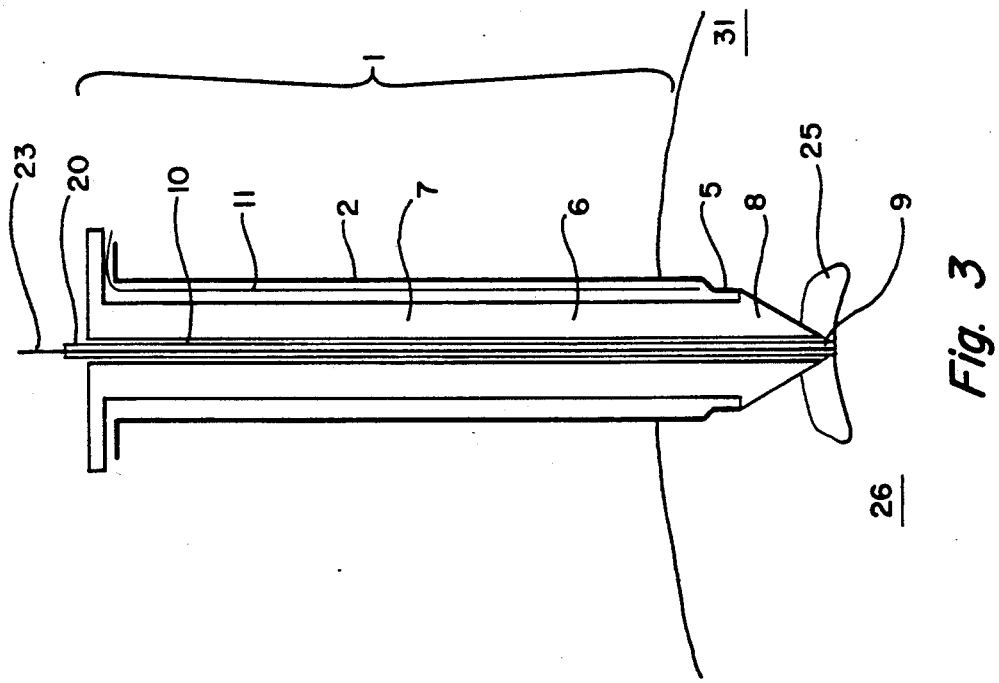
FIG. 3 is a view of the PEBB device which has been place over the localizing needle and which is entering the breast through a small incision.

In FIG. 3, when the biopsy is to be performed, the surgeon makes a small incision 25 in the breast skin 26 along the implanted localizing needle 20 which contains the hooked guide wire 23. The size of the incision must be sufficient to allow entry of the PEBB device 1, generally the incision is approximately 3 mm to 20 mm. Local anaesthesia can be utilized. The incision 25 provides passage for the PEBB device 1. The PEBB device 1 is passed over the localizing needle 20 and hooked guide wire 23 by inserting the localizing needle 20 and hooked guide wire 23 through the tapered pointed distal puncturing end 8 and hollow central shaft 10 of the stylet 6. The tapered pointed distal puncturing end 8 of the stylet 6 enters the breast 31 through the incision 25 that has been made.

Figure 4:
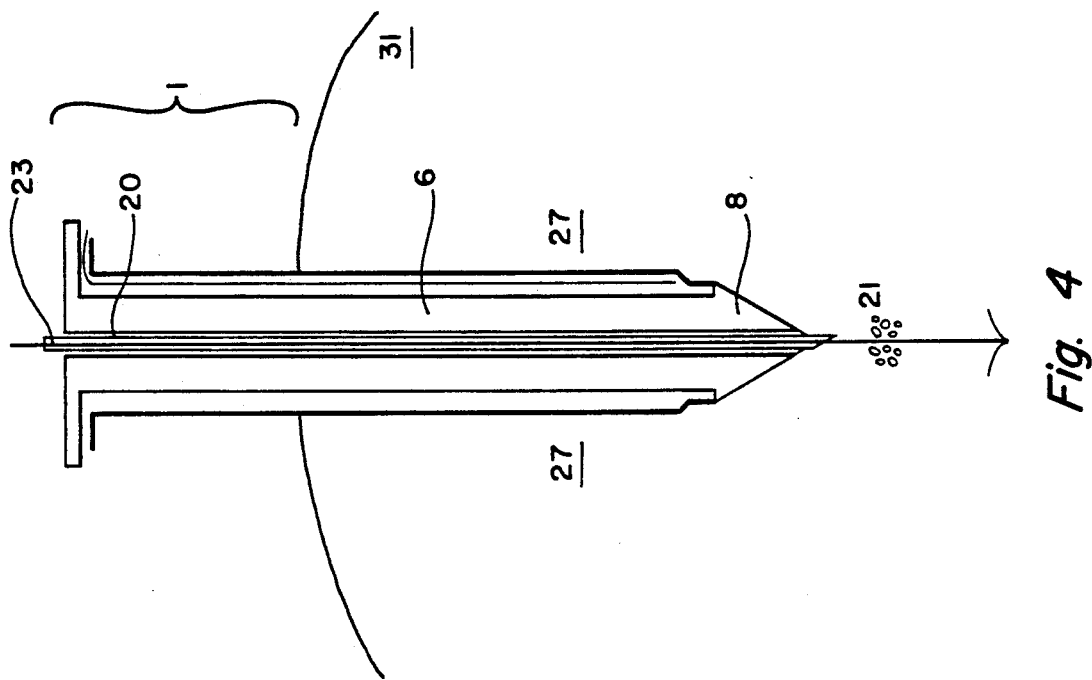
FIG. 4 is a view of the PEBB device passing into the breast along the localizing needle and stopping proximate the lesion and the hooked guide wire.

In FIG. 4, the tapered pointed distal puncturing end 8 of the stylet 6 bluntly separates the breast tissue 27. The PEB device 1 is advanced towards the lesion 21 and is stopped proximate the lesion 21, where the term "proximate" means a location before the lesion (i.e., under or above, depending on patient position). The PEBB device may be rotated while it is being advanced. The PEBB device 1 is generally stopped 1 to 4 cm before the lesion.

Figure 5:
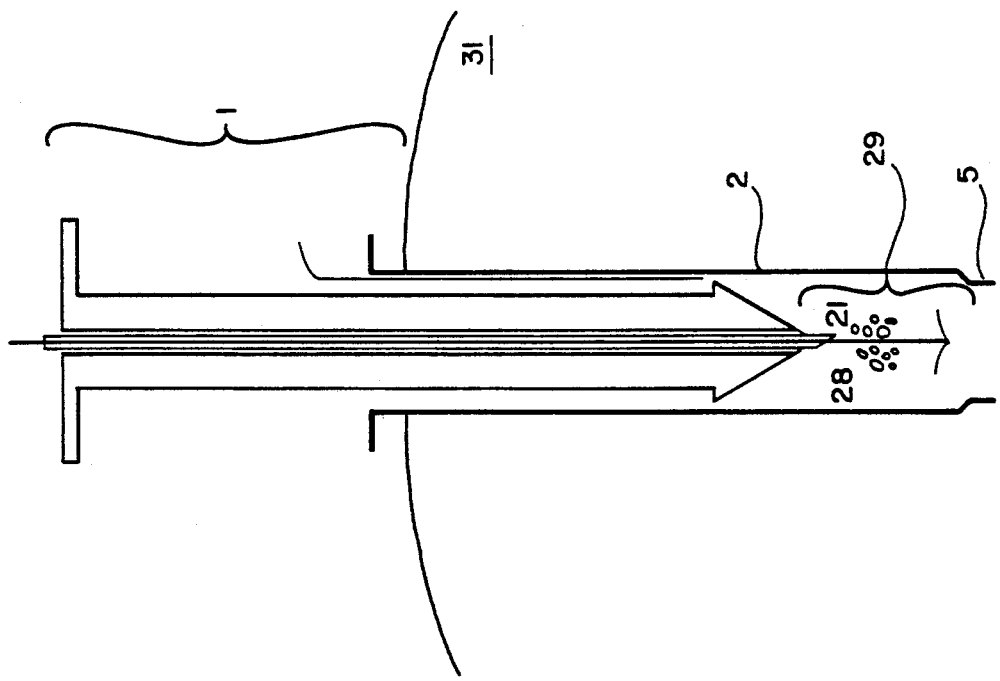
FIG. 5 is a view of the cannula of the PEBB device extended distal to the lesion and the hooked guide wire.

The position of the PEBB device 1 is confirmed by mammography. In FIG. 5, the cannula 2 of the PEBB device 1 is advanced distal the lesion 21, the sharp cutting surface 5 thereby cutting the breast tissue 28 surrounding the lesion 21 as the cannula 2 is being advanced. The cannula 2 can be rotated in order to aid cutting. Amammogram is conducted to confirm that the leson is in the chamber 29 formed by the cannula 2.

Figure 6:
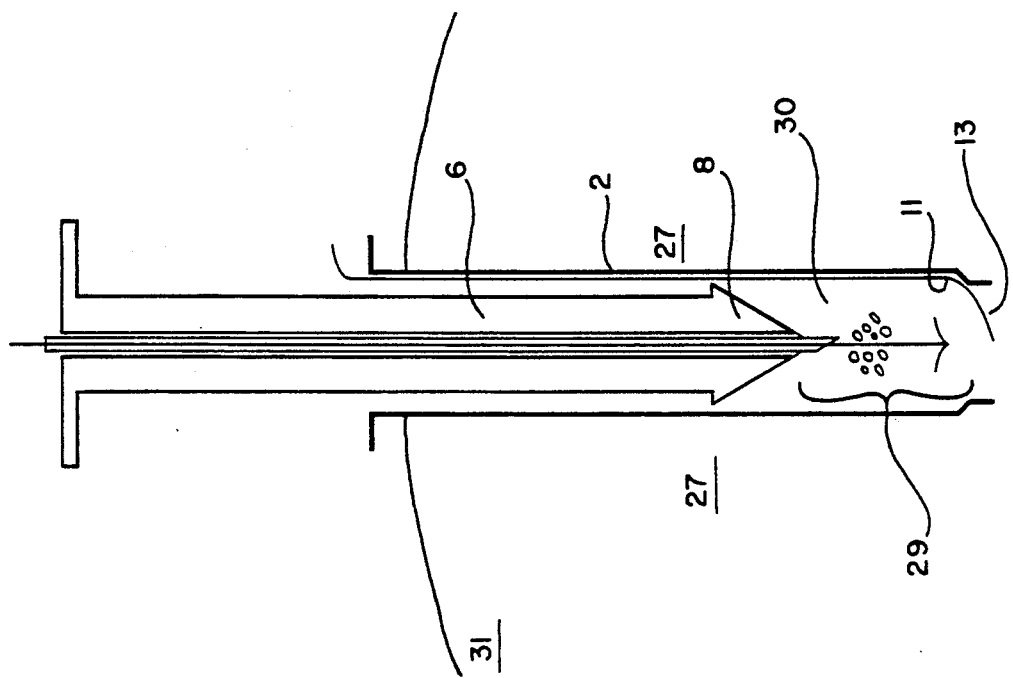
FIG. 6 is a view of the flexible steel cutting edge cutting the tissue distal the lesion and the hooked guide wire.

In FIG. 6, the descending element 11 is then pushed down in order for the flexible steel cutting edge 13 to internally cut the bottom of the biopsy specimen 30. The descending element 11 is rotated 360 degrees to completely cut the bottom of the biopsy specimen 30. The PEBB device 1 is then removed, taking along with it the biopsy specimen 30 in the chamber 29 formed by the cannula 2. Because the tapered pointed distal puncturing end 8 of the stylet 6 bluntly separates the breast tissue 27 from the incision 25 to the lesion 21, this intervening breast tissue 27 in not removed.

It will be appreciated that the instant specification and claims are set forth by way of illustration and not limitation and that various modifications and changes may be made without departing from the spirit and scope of the present invention.

What is claimed is:

1. A percutaneous excisional breast biopsy device comprising, in combination, a cannula member having upper proximal and lower distal ends and including a cannula open at the proximal and distal ends, said cannula having a sharp cutting surface at the distal end, and a stylet member having upper proximal and lower distal ends and including a stylet having a pointed distal end capable of spreading tissue, said stylet being slidable in said cannula for simultaneous insertion with said cannula, said stylet having a hollow central shaft capable of receiving a localizing needle, said device further comprising an additional means of cutting tissue and a localizing needle capable of being received into said stylet, said localizing needle capable of receiving a guide wire, said device further comprising a guide wire capable of being received into said localizing needle, said guide wire capable of holding tissue.

2. The device according to claim 1 wherein said guide wire has a hooked end.

* * * * *